(12) United States Patent
Knauf et al.

(10) Patent No.: US 9,227,909 B2
(45) Date of Patent: Jan. 5, 2016

(54) METHOD FOR THE CONTINUOUS PRODUCTION OF NITROBENZENE

(71) Applicant: Bayer MaterialScience AG, Leverkusen (DE)

(72) Inventors: Thomas Knauf, Lahntal (DE); Jurgen Munnig, Kaarst (DE); Joerg Schmiedler, Duisburg (DE)

(73) Assignee: Covestro Deutschland AG, Leverkusen (DE)

(*) Notice: Subject to any disclaimer, the term of this patent is extended or adjusted under 35 U.S.C. 154(b) by 69 days.

(21) Appl. No.: 14/046,068

(22) Filed: Oct. 4, 2013

(65) Prior Publication Data

US 2015/0099906 A1 Apr. 9, 2015
US 2015/0336875 A9 Nov. 26, 2015

(30) Foreign Application Priority Data

Oct. 10, 2012 (EP) .................................... 12188027

(51) Int. Cl.
*C07C 201/08* (2006.01)

(52) U.S. Cl.
CPC .................................... *C07C 201/08* (2013.01)

(58) Field of Classification Search
CPC ............................ C07C 201/06; C07C 201/08
USPC ....................................................... 568/939
See application file for complete search history.

(56) References Cited

U.S. PATENT DOCUMENTS

| | | | |
|---|---|---|---|
| 2,255,999 A | 9/1941 | Castner | |
| 2,739,174 A | 3/1956 | Ross | |
| 3,780,116 A | 12/1973 | Sahgal | |
| 4,310,500 A | 1/1982 | Langecker et al. | |
| 4,772,757 A | 9/1988 | Lailach et al. | |
| 5,313,009 A | 5/1994 | Guenkel et al. | |
| 5,334,781 A | 8/1994 | Kouwenhoven et al. | |
| 5,763,697 A | 6/1998 | Hermann et al. | |
| 5,963,878 A | 10/1999 | Brereton et al. | |
| 6,562,247 B2 | 5/2003 | Gillis et al. | |
| 7,326,816 B2 | 2/2008 | Knauf et al. | |
| 7,344,650 B2 | 3/2008 | Knauf et al. | |
| 7,763,759 B2 | 7/2010 | Knauf et al. | |
| 2013/0204043 A1 | 8/2013 | Knauf et al. | |

FOREIGN PATENT DOCUMENTS

| | | |
|---|---|---|
| EP | 0078247 B1 | 11/1985 |
| EP | 0436443 B1 | 4/1996 |
| WO | WO-2012013678 A2 * | 2/2012 |

OTHER PUBLICATIONS

Machine translation of WO 2012/013678 A2.*
Organic Chemical Manufacturing, vol. 7, Selected Processes, published by the United States Environmental Protection Agency, Dec. 1980.
Reinhard Billet, "Verdampfung und ihre technischen Anwendungen"; Verlag Chemie Weinheim—Deerfield Beach, Florida—Basel; 1981, section 4.1.2, pp. 208 to 230.

* cited by examiner

*Primary Examiner* — Yong Chu
*Assistant Examiner* — Ana Z Muresan
(74) *Attorney, Agent, or Firm* — Donald R. Palladino; Robert S. Klemz

(57) ABSTRACT

The present invention relates to a method for producing nitrobenzene, in which the waste gas streams accruing in the process and containing benzene and (traces of) nitrobenzene, possibly low- and medium-boiling components, possibly non-condensable gases and possibly water, optionally after removal of nitrogen oxides, are scrubbed in an absorption column with nitrobenzene, which comprises only very small amounts (maximum 50 ppm) of benzene and is distributed by means of a liquid distributor at a rate of 50 to 200 drip points per square meter, preferably 60 to 120 drip points per square meter, wherein (i) a liquid stream containing benzene and nitrobenzene, possibly organic low- and medium-boiling components and additionally containing sulfuric acid if sulfuric acid is used as the scrubbing agent and (ii) waste gas depleted in benzene and possibly in organic low- and medium-boiling components are obtained. A waste gas purified by the method according to the invention is particularly suitable for burning in a thermal exhaust air treatment process.

11 Claims, No Drawings

METHOD FOR THE CONTINUOUS PRODUCTION OF NITROBENZENE

CROSS-REFERENCE TO RELATED APPLICATIONS

The present application claims the right of priority under 35 U S.C. §119 (a)-(d) to European Application No. 12188027.2, filed Oct. 10, 2012

BACKGROUND OF THE INVENTION

Nitrobenzene is an important intermediate of the chemical industry, which is needed in particular for the production of aniline and hence for the production of methylene diphenyl diisocyanate (MIN) and of the polyurethanes based thereon.

The nitration of benzene with nitric acid to give a crude nitrobenzene has already been the subject of numerous publications and patent applications. The methods in common usage today correspond substantially to the concept of the adiabatic nitration of benzene with a mixture of sulfuric and nitric acid (known as a mixed acid). Such a method was first claimed in U.S. Pat. No. 2,256,999 and is described in its modern embodiments in EP 0 436 443 B1, EP 0 771 783 B1 and U.S. Pat. No. 6,562,247 B2, for example. The methods involving adiabatic reaction control are characterised in particular by the fact that no technical measures are taken to introduce heat into or to dissipate heat from the reaction mixture.

Isothermal methods for the nitration of benzene with mixed acid are also described, for example in EP 0 156 199 B1.

Methods for the nitration of benzene that manage without the use of sulfuric acid are described for example in U.S. Pat. No. 2,739,174 or U.S. Pat. No. 3,780,116.

Gas-phase methods for the nitration of benzene with nitric acid or nitrogen oxides are also possible in principle, but the yields that can be obtained with them are still low (EP 0 078 247 B1, EP 0 552 130 B1).

Crude nitrobenzene still contains as impurities water, benzene, nitrophenols and dinitrobenzene and—if nitrated with mixed acid—sulfuric acid, which are separated off by means of suitable processing methods such as scrubbing and distillation stages. A possible embodiment of this processing is described in EP 1 816 117 B1, where the nitrobenzene undergoes an acid scrubbing stage, an alkaline scrubbing stage, a neutral scrubbing stage and finally purification by distillation.

The processing of the alkaline waste water from the alkaline scrubbing stage is described in EP 1 593 654 A1, in which waste waters comprising aromatic nitro compounds are treated at elevated temperature and pressure in a method of thermal pressure decomposition. The waste waters treated by this method can be supplied directly to a biological sewage treatment plant without dilution.

The nitrogen oxides ($NO_x$ gases) formed during nitration can be treated with lye and washed out as sodium nitrate and nitrite as described in U.S. Pat. No. 5,313,009. In addition, carbon dioxide, which is formed in the nitration process, is also bound as sodium carbonate.

U.S. Pat. No. 5,963,878 discloses a method in which $NO_x$ gases obtained from strategic areas of the nitration system are brought into contact with air and water, for example in a unit having a packed bed, at elevated temperatures and under pressure, wherein the $NO_x$ gases are absorbed by the water, forming weak nitric acid. The weak nitric acid is returned to the reaction process. Carbon dioxide is not absorbed in an $NO_x$ gas scrubbing tower if the gas-scrubbing tower is operated in an acid mode. Clean, $NO_x$-free exhaust gas is released from the packed-bed unit into the environment.

In all of the referenced methods, therein no further treatment of the waste gases from nitration plants provided.

In WO2012013678A2 it is reported that countless studies in the past have aimed at improving the quality of the crude nitrobenzene and hence increasing the yield of benzene and nitric acid. Thanks to these developments, the modern adiabatic liquid-phase methods have advanced to such an extent that they all succeed in producing a crude nitrobenzene having a low content of secondary products, i.e. on average only between 100 ppm and 300 ppm of dinitrobenzene and between 1500 ppm and 2500 ppm of nitrophenols, wherein picric acid can make up a proportion of 10% to 50% of the nitrophenols.

"Organic Chemical Manufacturing, Volume 7, Selected Processes", published by the United States Environmental Protection Agency, discloses a method for purifying waste gases from a nitration process, in which the waste gases are purified in an absorption tower with nitrobenzene. No details are given of how nitrobenzene is distributed in the absorption tower. Furthermore, it is disclosed only that nitrobenzene from the nitrobenzene stripper can be used as the scrubbing solution. No details are given of the purity of this nitrobenzene.

DE-OS-29 21 487 discloses a method for removing volatile aromatic compounds from waste gases possibly containing nitrogen oxides and nitric acid, by treating the waste gases with a liquid nitration agent, for example a mixture of nitric and sulfuric acid. The use of nitrobenzene as a scrubbing solution is not disclosed.

When operating a nitration plant for producing nitrobenzene from benzene according to the prior art, it can be established that the isolated molar amount of the end product nitrobenzene and of the secondary products dinitrobenzene and nitrophenol that are inherent to the process is lower than the corresponding amount of benzene used. The outlet for this loss is clearly the waste gas from the production plant, which is undesirable from an ecological perspective. The loss is moreover also associated with economic disadvantages.

There was therefore a need to improve the existing nitration method to the effect that environmental pollution with organic components from the waste gas is reduced. It was moreover desirable to reduce environmental pollution in such a way that there are economic advantages associated with the reduction. It was desirable in particular to recycle benzene entrained in the waste gas.

SUMMARY OF THE INVENTION

Taking account of the above, the present invention provides a method for producing nitrobenzene comprising:
  a) nitrating benzene with nitric acid or mixtures of nitric acid and sulfuric acid and subsequent phase separation into an aqueous phase and crude nitrobenzene,
  b) scrubbing the crude nitrobenzene from step a) with an aqueous scrubbing solution in at least three scrubbing stages, each stage followed by separation of the scrubbing solution, wherein following separation of the scrubbing solution used in the final scrubbing stage a pre-purified nitrobenzene mixture is obtained which comprises at least benzene and water in addition to nitrobenzene,
  c) removing benzene and water from the pre-purified nitrobenzene mixture from step b) by distillation in a distillation apparatus to give purified nitrobenzene, wherein waste gas streams accrue in steps a) to c) which contain benzene and (traces of) nitrobenzene and possibly low and medium-boiling components, possibly non-condensable gases and possibly water; and, optionally after removal of nitrogen oxides, d) scrubbing the waste gas streams countercurrently in an absorption column with nitrobenzene, which has a benzene content of <50 ppm, relative to the total mass of nitrobenzene, and is distributed by means of a liquid distributor at a rate of 50 to 200 drip points per square meter, wherein (i) a liquid stream containing benzene and nitrobenzene and (ii) a nitrobenzene-depleted waste gas are obtained.

DETAILED DESCRIPTION OF THE PREFERRED EMBODIMENTS

In the context of this invention the word "a" in connection with countable quantities is to be understood as meaning "one" only if expressly stated (for example by means of the expression "precisely one"). For example, the expression "an absorption column" does not exclude the possibility of the presence of a plurality of absorption columns (connected in series or in parallel).

In the context of this invention the term "low-boiling components" denotes all compounds and azeotropically boiling mixtures of compounds whose boiling points are below that of benzene under normal pressure (1013 mbar). Typical low-boiling components are n-heptane, dimethyl cyclopentane, 3-ethyl pentane, cyclohexane, the isomeric dimethyl pentanes, n-hexane, cyclopentane and n-pentane. In the context of this invention the term "medium-boiling components" denotes all compounds and azeotropically boiling mixtures of compounds whose boiling points are above that of benzene under normal pressure (1013 mbar) but below that of nitrobenzene under normal pressure (1013 mbar). Typical medium-boiling components are trimethyl cyclopentane, methyl cyclohexane, ethyl cyclopentane, bicycloheptane and octane.

Within the context of the present inventions non-condensable gases are understood to be substances which under normal conditions are in gaseous form and cannot be liquefied with condensers conventionally used in industry (temperatures down to −20° C.) under normal pressure. Typical examples are nitrogen oxides ($NO_x$) and carbon dioxide.

The invention is explained in detail below. Different embodiments can be freely combined with one another unless clearly indicated to the contrary to the person skilled in the art from the context.

Step a) of the method according to the invention can in principle be carried out by all methods of benzene nitration known in the prior art. The precise nature of the nitration method is not substantial to the invention. An adiabatic process control is preferred, in which a mixture of nitric and sulfuric acid is used with a stoichiometric excess of benzene relative to nitric acid, wherein after the reaction the sulfuric acid used in excess is separated off from the crude product, concentrated and returned to the nitration process ("recycled sulfuric acid"). The excess benzene is also returned to the nitration process ("recycled benzene"). A process control as described in DE 10 2008 048713 A1, in particular in paragraph [0024], to which reference is expressly made here, is particularly preferred. An isothermal process control is however also possible in principle.

In step b) of the method according to the invention the individual scrubbing stages can be performed in principle in any order. The following order is preferred, however:

(1) scrubbing with a non-alkaline aqueous scrubbing solution
(2) alkaline scrubbing with an aqueous base solution, preferably an alkali metal or alkaline-earth metal hydroxide solution, particularly preferably with a sodium hydroxide solution
(3) neutral scrubbing with water.

The acid residues (i.e. sulfuric acid) comprised in the crude nitrobenzene are washed out in step b) (1); this process step is therefore also described as an acid scrubbing stage.

Step b) particularly preferably takes place according to the procedure described in paragraphs [0008] to [0012] of EP 1 816 117 B1, to which reference is expressly made here. An electrophoresis is particularly preferably used in the neutral scrubbing stage in step b), as described in EP 1 816 117 B1, paragraph [0013], to which reference is expressly made here.

In step c) of the method according to the invention unreacted benzene and residual amounts of water are preferably distilled off from nitrobenzene in a rectifying column. In this distillation stage purified nitrobenzene is precipitated as the bottom product of the distillation column. It is moreover possible, and for many downstream applications preferable, to purify this purified nitrobenzene accruing as the bottom product still further, by distilling (evaporating and recondensing) the nitrobenzene itself. Highly pure nitrobenzene is obtained in this way. A rectifying column as preferably used as the distillation apparatus for this purpose, in other words an apparatus in which at least a theoretical separation stage is performed and in which a liquid reflux stream is fed into the top of the column. The highly pure nitrobenzene is preferably removed from the top of a distillation column. Removal of a side stream is likewise conceivable, however. This ultrapurification is particularly preferably performed by the procedure described in WO 2012/013678 A2, to which reference is expressly made here.

In all of the process steps described thus far, gaseous waste gas streams accrue. Process waste gases are preferably removed at the phase separation apparatus of step a), the acid, alkaline and neutral scrubbing stages in step b), the receiver tank for recycled sulfuric acid and recycled benzene (see above, adiabatic process control of step a)), the crude and pure nitrobenzene tanks and the waste water tanks from the scrubbing stage in step b), and preferably purified before step d) is performed. Waste gases are preferably also obtained in the vacuum systems of the evaporator used to concentrate the recycled sulfuric acid (adiabatic process control, see above) and the distillation apparatus for purifying nitrobenzene (step c)). Condensate from the vacuum systems is preferably used further in the scrubbing stages. The individual waste gas streams comprise in varying composition benzene, nitrobenzene, possibly low- and medium-boiling components, possibly non-condensable gases ($NO_x$, carbon dioxide) and possibly water. These waste gas streams are scrubbed in an absorption column in step d). This scrubbing stage in the absorption column can preferably be preceded by a step d.0), in which the waste gases from steps a) to c) are freed from nitrogen oxides, either separately or preferably after combining the individual waste gas streams to form a complete waste gas stream. The removal of nitrogen oxides from the waste gas stream(s) can be performed by any of the methods known from the prior art. The use of an NOx absorber as described in U.S. Pat. No. 5,963,878, in particular in column 2, line 12 to column 3, line 27, is preferred. Alternatively, a nitrogen oxide separation that may possibly be required can also be designed in a step d.1) subsequent to step d), as described above for step d.0). This is particularly preferable as a means of avoiding the explosive limits of the benzene/oxygen waste gas mixture, which would arise on introducing oxygen into the waste gas stream for NOx absorption.

In step d) of the method according to the invention, the waste gas stream(s), which have optionally been freed from nitrogen oxides in step d.0), are scrubbed in an absorption column with nitrobenzene having a low benzene content, in order to wash out entrained benzene and possibly any other organic constituents (low- and medium-boiling components). Irrespective of whether step d.0) is performed or not, it is preferable for all waste gas streams to be combined into a single complete waste gas stream before the scrubbing stage in step d). If the waste gas streams from steps a) to c) have not already been combined before step d.0), all waste gas streams obtained from step d.0) and freed from nitrogen oxides are preferably combined before scrubbing step d) is performed.

The pressure in the absorption column used in step d) is preferably chosen such that benzene and possibly low- and medium-boiling components are washed out in the optimal manner. The invention therefore relates in particular also to a method in which step d) is operated under an absolute pressure of 900 mbar to 980 mbar, preferably 920 mbar to 960 mbar. The pressure is preferably measured at the entrance to the absorption column.

An important criterion for the nitrobenzene stream for use as the scrubbing solution in step d) is its benzene content. According to the invention a nitrobenzene having a benzene content (determined by gas chromatography) of <50 ppm, preferably <20 ppm, particularly preferably <10 ppm, relative in each case to the total mass of nitrobenzene, is used as the scrubbing solution.

The temperature of the scrubbing nitrobenzene in the absorption column in step e) is preferably chosen such that benzene and possibly low- and medium-boiling components are washed out with nitrobenzene in the optimal manner. The invention thus also relates in particular to a method in which the nitrobenzene from step c) used as the scrubbing solution in step d) has a temperature of 20° C. to 75° C., preferably 25° C. to 60°, particularly preferably 30° C. to 45° C. The temperature of the scrubbing nitrobenzene is preferably measured in the feeder pipe ahead of the absorption column. The vapour temperature at the outlet from the absorption column is preferably 20° C. to 75° C., particularly preferably 20° C. to 50° C., most particularly preferably 20° C. to 40° C., and is measured in the vapour line.

According to the invention a direct condensation apparatus is used in step d), in which benzene and possibly low- and medium-boiling components from the waste gas are absorbed with scrubbing nitrobenzene and then the mixture thus obtained, containing nitrobenzene, benzene and possibly low- and medium-boiling components, is removed from the absorption column. The procedure according to the invention not only allows the effective removal of benzene from the waste gas but moreover also leads to a sharp reduction in the content of low- and medium-boiling components in the waste gas, in particular of aliphatic organic compounds. This is achieved through the use of a liquid distributor having a drip point density of 50 to 200 drip points per square meter, preferably 60 to 120 drip points per square meter. Too large a number of drip points means too great an additional demand for absorbing agent, which leads to an elevated circulation in the rectifying column. Too small a number of drip points results in too low an absorption efficiency. Furthermore, the extremely low benzene content in the scrubbing nitrobenzene is substantial. The benzene content according to the invention of <50 ppm, preferably <20 ppm and particularly preferably <10 ppm is lower than that permitted by the specification for the nitrobenzene conventionally used for aniline production (the principal application area for nitrobenzene). Purified nitrobenzene from step c) is preferably used as the scrubbing solution. In this case step c) must be designed such that the requirements according to the invention for the residual benzene content of the nitrobenzene are complied with. This is preferably achieved by performing the distillation in step c) under an absolute pressure at the top of the distillation column of 220 mbar to 480 mbar, preferably 270 mbar to 430 mbar, particularly preferably 320 mbar to 380 mbar, and at a temperature at the bottom of the distillation column of 100° C. to 200° C., preferably 120° C. to 190° C., particularly preferably 160° C. to 180° C. The distillation column used in step c) preferably has a forced-circulation reboiler, in which the distillation bottoms are heated to the specified temperature values by steam heating. These measures also ensure that the residual water content of the nitrobenzene is <100 ppm, preferably <70 ppm, particularly preferably <40 ppm, relative in each case to the total mass of nitrobenzene.

Suitable apparatus is described for example in Reinhard Billet, "Verdampfung und ihre technischen Anwendungen"; Verlag Chemie Weinheim—Deerfield Beach, Florida—Basel; 1981, section 412, pages 208 to 230.

The liquid stream obtained in step d) containing benzene and possibly low- and medium-boiling components and scrubbing solution, preferably purified nitrobenzene from step c), can be burned or preferably recycled in the nitration process or most preferably processed.

A waste gas purified by the method according to the invention and obtained in step d) is particularly suitable for burning in a thermal exhaust air treatment process.

A distillation process in which the organic low-boiling components are separated from benzene and nitrobenzene is suitable for a processing stage. The low-boiling components are burned or are returned to a petrochemical process. The mixture of nitrobenzene and benzene is returned to the nitration process, preferably to the crude nitrobenzene tank, particularly preferably to the crude nitrobenzene scrubbing stage in step b), most particularly preferably to the crude nitrobenzene acid scrubbing stage (step b) (1)). The present invention therefore also provides a method in which the liquid stream containing benzene and nitrobenzene obtained in step d)

e) is distilled so as separately to obtain benzene and nitrobenzene or to obtain a mixture of benzene and nitrobenzene, preferably to obtain a mixture of benzene and nitrobenzene.

In particular, the invention also provides a method in which the distillation in step e) is operated such that a mixture of benzene and nitrobenzene is obtained which f) is returned to step b), preferably to the first scrubbing stage of step b).

A preferred embodiment for operating an absorption column with a multistage condensation is described below:

All waste gases from the plant are collected and sent under controlled pressure to a waste gas scrubbing stage, which can be operated both under overpressure and under reduced pressure. The waste gas comprises nitrogen oxides, benzene, further organic constituents such as low- and medium-boiling components and small amounts of nitrobenzene along with nitrogen from pressure holding systems in the nitration plant and tank inserting systems.

The waste gas comprising low-boiling components, benzene, nitrobenzene, medium-boiling components (which boil between benzene and nitrobenzene) and nitrogen oxides is fed into the waste gas scrubbing unit from below under slightly reduced pressure of 900 mbar to 1000 mbar. The waste gas has a temperature of 20° C. to 75° C. The waste gas scrubbing unit, which is designed as a direct condensation, is operated with purified nitrobenzene from step c), which is distributed by means of a liquid distributor at a rate of 50 to 200 drip points per square meter, preferably 60 to 120 drip points per square meter. The purified nitrobenzene, which has a temperature of 20° C. to 75° C., condenses low-boiling components, benzene, medium-boiling components and traces of nitrobenzene vapours from the waste gas. The pure nitrobenzene is atomised countercurrently through a single-substance nozzle with a droplet spectrum of 0.2 mm to 2.0 mm. The exchange of substances is ensured by means of a structured packing or packed column packing. The residence time of the gas stream in the absorption column is less than 30 seconds. The exchange surface thus produced is therefore sufficient to achieve an effective absorption of the waste gases. 0.5 to 5 tonnes per hour of liquid phase from the absorption column, comprising nitrobenzene, medium-boiling components, benzene, low-boiling components and traces of nitrogen oxide and nitrogen, are returned to the scrubbing stage after step b) (1) (acid scrubbing stage). Approximately 10 to 50 kg per hour of benzene are recovered in this way. The liquid phase can optionally be distilled to remove undesired low-boiling components before being returned to the acid scrubbing stage.

The waste gas purified in this way can be sent for thermal exhaust air treatment without any difficulty.

EXAMPLES

Gas chromatography was used for analysis of the waste gas streams in all examples. The organic components were identified by GC-MS (mass spectrometry).

Example 1 (Comparative Example)

Untreated Waste Gas

Pre-purified nitrobenzene was first produced according to steps a) to b) of the method according to the invention and in step c) it was freed from benzene, water and low-boiling components in a rectifying column. The purified nitrobenzene is removed as the bottom product. The waste gas accruing in the nitration plant and the associated tank containers is collected in a water-operated waste gas exchange system and then sent for thermal exhaust air treatment. The nitration plant is operated with a production load of 42 tonnes of nitrobenzene per hour. The waste gas stream is approximately 150 m$^3$ per hour and comprises approximately 160 g/m$^3$ of benzene. The benzene losses via the discharged waste gas amount to 24 kg of benzene per hour. This represents 0.09% of the benzene used.

Example 2 (Comparative Example)

Removal of Benzene from the Waste Gas with Water in a Waste Gas Scrubbing Process with Single-Stage Condensation Pre-purified nitrobenzene was first produced according to steps a) to b) of the method according to the invention and in step c) it was freed from benzene, water and low-boiling components in a rectifying column. The purified nitrobenzene is removed as the bottom product. The waste gas accruing in the nitration plant and the associated tank containers is collected in a water-operated waste gas exchange system and then sent to a waste gas scrubber as described above. The nitration plant is operated with a production load of 42 tonnes of nitrobenzene per hour. The waste gas stream is approximately 150 m$^3$ per hour and comprises approximately 160 g/m$^3$ of benzene. The organic components contained in the waste gas are precipitated with water, which is taken from the acid scrubbing stage and has a temperature of 40° C.

The amount of water used is 2 tonnes per hour. The water is atomised and is distributed by means of a liquid distributor at a rate of 80 drip points per square meter. 3 kg of benzene are recovered per hour. The waste gas treated in this way, which still comprises approximately 140 g/m$^3$ of benzene, is sent for thermal exhaust air treatment. The benzene losses via the exhaust rail amount to 21 kg of benzene per hour. This represents 0.079% of the benzene used.

Example 3 (Comparative Example)

Removal of Benzene from the Waste Gas with Crude Nitrobenzene in a Waste as Scrubbing Process with Single-Stage Condensation Pre-purified nitrobenzene was first produced according to steps a) to b) of the method according to the invention and in step c) it was freed from low-boiling components in a rectifying column. The purified nitrobenzene is removed as the bottom product. The waste gas accruing in the nitration plant and the associated tank containers is collected in a water-operated waste gas exchange system and then sent to a waste gas scrubber as described above. The nitration plant is operated with a production load of 42 tonnes per hour. The waste gas stream is 150 m$^3$ per hour and comprises approximately 160 g/m$^3$ of benzene. The organic components contained in the waste gas are precipitated with crude nitrobenzene, which is taken from the crude nitrobenzene tank, comprises 7.2 mass % of benzene and has a temperature of 36° C. The amount of crude nitrobenzene used amounts to 1.1 tonnes per hour. The crude nitrobenzene is atomised and is distributed by means of a liquid distributor at a rate of 80 drip points per square meter. More benzene (approximately 240 g/m$^3$) per hour was found in the waste gas after the waste gas scrubber than before it. The waste gas treated in this way is sent for thermal exhaust air treatment.

Example 4 (Comparative Example)

Removal of Benzene from the Waste Gas with Purified Nitrobenzene in Waste Gas Scrubbing Process with a Single-Stage Absorption Column Pre-purified nitrobenzene was first produced according to steps a) to b) of the method according to the invention and in step c) it was freed from low-boiling components in a rectifying column. The purified nitrobenzene is removed as the bottom product. The waste gas accruing in the nitration plant and the associated tank containers is collected in a waste gas collecting line and sent to a waste gas scrubber. The nitration plant is operated with a production load of 42 tonnes per hour. The waste gas stream is approximately 150 m$^3$ per hour and comprises approximately 160 g/m$^3$ of benzene. The organic components contained in the waste gas are precipitated with purified nitrobenzene having a benzene content of 100 ppm, which is taken from the "pure nitrobenzene tank" and has a temperature of 38° C. 1.1 tonnes of purified nitrobenzene are atomised per hour and are distributed by means of a liquid distributor at a rate of 50 drip points per square meter. 13.5 kg of benzene are recovered per hour. The waste gas treated in this way is sent for thermal exhaust air treatment. The benzene losses via the thermal exhaust air treatment amount to 10.5 kg of benzene per hour. This represents 0.039% of the benzene used.

TABLE 1

Analysis of the waste gas stream before and after the waste gas scrubber in Example 4:

| | Substance | |
|---|---|---|
| | Nitrobenzene | Benzene |
| Amount before waste gas scrubber [g/m³ waste gas] | 0.021 | 160 |
| Amount after waste gas scrubber [g/m³ waste gas] | 0.132 | 71 |

Most of the nitrobenzene contained in the waste gas after the waste gas scrubbing stage is removed from the waste gas in an NOx absorption stage (step d.1)).

Example 5 (According to the Invention)

Removal of Benzene from the Waste Gas with Purified Nitrobenzene in a Waste Gas Scrubbing Process with a Single-Stage Absorption Column Pre-purified nitrobenzene was first produced according to steps a) to b) of the method according to the invention and in step c) it was freed from low-boiling components in a rectifying column. The purified nitrobenzene is removed as the bottom product. The waste gas accruing in the nitration plant and the associated tank containers is collected in a waste gas collecting line and sent to a waste gas scrubber. The nitration plant is operated with a production load of 42 tonnes per hour. The waste gas stream is approximately 150 m³ per hour and comprises approximately 160 g/m³ of benzene. The organic components contained in the waste gas are precipitated with purified nitrobenzene having a benzene content of 5 ppm, which is taken from the "pure nitrobenzene tank" and has a temperature of 38° C. 1.1 tonnes of purified nitrobenzene are atomised per hour and are distributed by means of a liquid distributor at a rate of 50 drip points per square meter. 23.5 kg of benzene are recovered per hour. The waste gas treated in this way is sent for thermal exhaust air treatment. The benzene losses via the thermal exhaust air treatment amount to 0.5 kg of benzene per hour. This represents 0.00187% of the benzene used.

TABLE 2

Analysis of the waste gas stream before and after the waste gas scrubber in Example 5:

| | Substance | |
|---|---|---|
| | Nitrobenzene | Benzene |
| Amount before waste gas scrubber [g/m³ waste gas] | 0.021 | 160 |
| Amount after waste gas scrubber [g/m³ waste gas] | 0.132 | 2 |

Most of the nitrobenzene contained in the waste gas after the waste gas scrubbing stage is removed from the waste gas in an NOx absorption stage (step d.1)).

Example 6 (According to the Invention)

Removal of Benzene from the Waste Gas with Purified Nitrobenzene in a Waste Gas Scrubbing Process with a Six-Stage Absorption Column Pre-purified nitrobenzene was first produced according to steps a) to b) of the method according to the invention and in step c) it was freed from low-boiling components in a rectifying column. The purified nitrobenzene is removed as the bottom product. The waste gas accruing in the nitration plant and the associated tank containers is collected in a waste gas collecting line and sent to a waste gas scrubber. The nitration plant is operated with a production load of 42 tonnes of nitrobenzene per hour. The waste gas stream is approximately 150 m³ per hour and comprises approximately 160 g/m³ of benzene. The organic components contained in the waste gas are precipitated in a waste gas scrubber (absorption column) with six-stage condensation using purified nitrobenzene having a benzene content of 5 ppm, which is taken from the "pure nitrobenzene tank" and has a temperature of 39° C. 1.1 tonnes of nitrobenzene are atomised per hour and are distributed by means of a liquid distributor at a rate of 120 drip points per square meter. 23.99 kg of benzene are recovered per hour. The waste gas treated in this way is sent for thermal exhaust air treatment. The benzene losses via the thermal exhaust air treatment amount to (0.01 kg of benzene per hour. This represents 0.000037% of the benzene used.

This example shows that with identical purity of the scrubbing nitrobenzene that is used, the design of the liquid distributor is of great importance in reducing the benzene content in the waste gas.

TABLE 3

Analysis of the waste gas stream before and after the organic component scrubber in Example 6:

| | Substance | |
|---|---|---|
| | Nitrobenzene | Benzene |
| Amount before waste gas scrubber [g/m³ waste gas] | 0.019 | 160 |
| Amount after waste gas scrubber [g/m³ waste gas] | 0.129 | 0.06 |

What is claimed is:

1. A method for producing nitrobenzene, comprising
   a) nitrating benzene with nitric acid or mixtures of nitric acid and sulfuric acid and subsequent phase separation into an aqueous phase and crude nitrobenzene,
   b) scrubbing the crude nitrobenzene from step a) with an aqueous scrubbing solution in at least three scrubbing stages, each stage followed by separation of the scrubbing solution wherein following separation of the scrubbing solution used in the final scrubbing stage a pre-purified nitrobenzene mixture is obtained which comprises at least benzene and water in addition to nitrobenzene,
   c) removing benzene and water from the pre-purified nitrobenzene mixture from step b) by distillation in a distillation apparatus to give purified nitrobenzene,
   wherein waste gas streams accrue in steps a) to c) which contain benzene and nitrobenzene, and
   d) scrubbing the waste gas streams countercurrently in an absorption column with nitrobenzene, which has a benzene content of <50 ppm, relative to the total mass of nitrobenzene, and is distributed by means of a liquid distributor at a rate of 50 to 200 drip points per square meter, wherein (i) a liquid stream containing benzene and nitrobenzene and (ii) a nitrobenzene-depleted waste gas are obtained.

2. The method according to claim 1, wherein step d) is performed under an absolute pressure of about 900 mbar to about 980 mbar.

3. The method according to one of claims 1 or 2, wherein purified nitrobenzene from step c) is used as the scrubbing solution in step d).

4. The method according to claim 3, wherein the distillation in step c) is operated under an absolute pressure at the top of the distillation column of about 220 mbar to about 480 mbar and at a temperature at the bottom of the distillation column of about 100° C. to about 200° C.

5. The method according to claim 3, wherein the distillation in step c) is operated under an absolute pressure at the top of the distillation column of about 270 mbar to about 430 mbar and at a temperature at the bottom of the distillation column of about 120° C. to about 190° C., and wherein the purified nitrobenzene used as the scrubbing solution in step d) has a benzene content of <20 ppm, relative to the total mass of purified nitrobenzene.

6. The method according to claim 3, wherein the distillation in step c) is operated under an absolute pressure at the top of the distillation column of about 320 mbar to about 380 mbar and at a temperature at the bottom of the distillation column of about 160° C. to about 180° C., and wherein the purified nitrobenzene used as the scrubbing solution in step d) has a benzene content of <10 ppm, relative to the mass of purified nitrobenzene.

7. The method according to one of claims 3 to 6, wherein the nitrobenzene from step c) used as the scrubbing solution in step d) has a temperature of about 20° C. to about 75° C.

8. The method according to one of claims 1 to 7, wherein the absorption column is operated in such a way that the gaseous vapours that are discharged have a temperature of about 20° C. to about 75° C.

9. The method according to one of claims 1 to 8, wherein the liquid distributor used in step d) has a drip point density of about 60 to about 120 drip points per square meter.

10. The method according to one of claims 1 to 9, further comprising
 e) distilling the liquid stream obtained in step d) so as to obtain a liquid selected from the group consisting of benzene, nitrobenzene and a mixture of benzene and nitrobenzene.

11. The method according to claim 10, further comprising
 f) returning the mixture of benzene and nitrobenzene to step b.

* * * * *

UNITED STATES PATENT AND TRADEMARK OFFICE
CERTIFICATE OF CORRECTION

| | | |
|---|---|---|
| PATENT NO. | : 9,227,909 B2 | Page 1 of 1 |
| APPLICATION NO. | : 14/046068 | |
| DATED | : January 5, 2016 | |
| INVENTOR(S) | : Thomas Knauf et al. | |

It is certified that error appears in the above-identified patent and that said Letters Patent is hereby corrected as shown below:

Title page
In the Inventors item (72), Inventor Thomas Knauf's city of residence should be changed from "Lahntal (DE)" to "Dormagen (DE)"

Signed and Sealed this
Nineteenth Day of April, 2016

Michelle K. Lee
*Director of the United States Patent and Trademark Office*